United States Patent [19]
Mautner et al.

[11] Patent Number: 5,877,337
[45] Date of Patent: Mar. 2, 1999

[54] PROCESS FOR PREPARING ALKYLCHLOROSILANES FROM THE RESIDUES OF DIRECT SYNTHESIS OF ALKYLCHLOROSILANES

[75] Inventors: Konrad Mautner; Anton Schinabeck, both of Burghausen; Herbert Straussberger, Mehring, all of Germany

[73] Assignee: Wacker-Chemie GmbH, Germany

[21] Appl. No.: 12,365

[22] Filed: Jan. 23, 1998

[30] Foreign Application Priority Data

Mar. 20, 1997 [DE] Germany .................. 197 11 693.0

[51] Int. Cl.⁶ .................. C07F 7/08; C07F 7/16
[52] U.S. Cl. .................. 556/466; 556/467; 556/468; 556/472
[58] Field of Search .................. 556/466, 467, 556/468, 472

[56] References Cited

U.S. PATENT DOCUMENTS

| | | |
|---|---|---|
| 2,681,355 | 6/1954 | Barry et al. . |
| 2,709,176 | 5/1955 | Bluestein . |
| 5,288,892 | 2/1994 | Padaly et al. . |
| 5,321,147 | 6/1994 | Chadwick et al. ................ 556/466 |
| 5,326,896 | 7/1994 | Chadwick et al. ................ 556/466 |
| 5,502,230 | 3/1996 | Mautner et al. . |
| 5,627,298 | 5/1997 | Freeburne et al. ................ 556/466 |
| 5,629,438 | 5/1997 | Freeburne et al. ................ 556/466 |

FOREIGN PATENT DOCUMENTS 0574912   12/1993   European Pat. Off. .

Primary Examiner—Paul F. Shaver
Attorney, Agent, or Firm—Brooks & Kushman P.C.

[57] ABSTRACT

Alkylchlorosilanes are prepared continuously from the residue of direct synthesis of alkylchlorosilanes containing liquid constituents with a boiling point of at least 70° C. at 1013 hPa and solid constituents, by heating the residue with hydrogen chloride at temperatures of from 300° C. to 800° C. in a tubular reactor with internals which can be rotated.

8 Claims, No Drawings

PROCESS FOR PREPARING ALKYLCHLOROSILANES FROM THE RESIDUES OF DIRECT SYNTHESIS OF ALKYLCHLOROSILANES

TECHNICAL FIELD

The invention relates to a continuous process for preparing alkylchlorosilanes, in which the residues of direct synthesis of alkylchlorosilanes are cleaved thermally using hydrogen chloride.

DESCRIPTION OF THE RELATED ART

During the direct synthesis of alkylchlorosilanes of the general formula $R_aH_bSiCl_{4-a-b}$, in which a is 1, 2, 3 or 4 and b is 0, 1 or 2, from metallic silicon and alkyl chlorides R-Cl, where R is an alkyl radical; oligosilanes, carbosilanes, siloxanes and high-boiling cracking products are produced as byproducts. The distillation residue moreover contains solids from the direct synthesis, which, as fines, are not retained even by cyclones and filters. The solids are composed of silicon, metal chlorides, e.g. $AlCl_3$, metal silicides and soot.

The oligosilanes, in particular disilanes of the general formula $R_cCl_{6-c}Si_2$, in which c is from 0 to 6, make up the predominant part of the residues. Disilanes which are low in methyl may be converted to monosilanes using hydrogen chloride in the presence of nitrogen-containing catalysts; this is described, for example, in U.S. Pat. No. 2,709,176. U.S. Pat. No. 5,502,230 describes a process for reclaiming disilanes which are rich in methyl by cleaving these using HCl in the presence of a catalyst composed of palladium (0) or platinum (0) and a specific organic nitrogen- or phosphorus-containing compound. The various disilanes can be cleaved only by using different catalyst types. The disilanes must moreover be first separated previously from the solid residues, since components of these residues, for example, aluminum chloride, act as catalyst poisons.

U.S. Pat. No. 2,681,355 describes a continuous, catalyst-free and purely thermal process in which residues with boiling points above 70° C. from direct synthesis of methylchlorosilanes are reacted with hydrogen chloride at temperatures of from 400° C. to 900° C. in a tube without packing, giving monomeric silanes. When residues containing solids are reacted, there is a build-up in the reactor tube.

SUMMARY OF THE INVENTION

It would be desirable to provide a process which is easily implemented and which, at low pressures, can treat even solids-containing residues of direct synthesis of alkylchlorosilanes, and convert the organosilicon fractions into useful silanes. The present invention provides a continuous process for preparing alkylchlorosilanes from the residues of direct synthesis of alkylchlorosilanes, these residues containing liquid constituents with a boiling point of at least 70° C. at 1013 hPa and also containing solids, by heating the residues with hydrogen chloride at temperatures of from 300° to 800° C. in a tubular reactor with internals which can be rotated. The rotation of the internals shears off baked-on material resulting from carbonization or from the solid fractions on the reactor walls. This prevents a build-up in the reactor, making it possible to operate the process continuously for long periods.

DETAILED DESCRIPTION OF THE INVENTION

Alkylchlorosilanes preferably prepared are those of the general formula given above in which R is methyl, ethyl, butyl or propyl, in particular methyl.

The residues of direct synthesis preferably have liquid constituents with a boiling point, at 1013 hPa, of at least 80° C., in particular at least 100° C.

The residues are preferably fed into a tubular reactor together with hydrogen chloride. Mixing may have taken place previously or may take place for the first time in the reactor. The amount of hydrogen chloride used is at least the molar equivalent of the disilanes contained in the residue, but not more than 10 times the molar amount. Preference is given to the use of from 1.1 to 2 times the molar amount. The residue and the hydrogen chloride may either be preheated or metered into the reactor at ambient temperature, the streams being preferably metered in continuously. If preheating is used, the residue may also be metered in as a gasliquid mixture.

The tube-shaped reactor is composed of a jacket, which can be heated directly or indirectly to the desired operating temperature, for example, up to 800° C. Non-limiting means of heating are the use of heating oils stable at high temperatures, electrical resistance heating, induction heating, and combinations of these. The reactor is operated at from 300° C. to 800° C., preferably from 500° C. to 650° C. The pressure is preferably from 500 hPa to 10,000 hPa, in particular from 1000 hPa to 3000 hPa.

One or more rotatable elements are built into the reactor, and these shear off residues and crusts from the reactor wall. Preference is given to rigid rotors with at least two blades. In the simplest case, the reactor is very similar to a thin-film evaporator with a rotor. The length to diameter ratio of the reactor is at least 0.5, preferably at least 5. The reactor may be operated in the horizontal or the vertical position, preferably the latter.

The residue and the hydrogen chloride may be metered in countercurrently or concurrently. If desired, there may be more than one location, distributed along the length of the reactor, for metering-in one or more streams.

A positive side-effect of the heat treatment is sintering of the solid particles, as a result of which it is possible to convert difficult-to-filter, possibly colloidally distributed solids into fractions which can be filtered.

The mixture emerging from the reactor is condensed and, if desired, freed from solids, and can be reintroduced to the alkylchlorosilane mixture produced in direct synthesis, or else can be separated into pure substances.

In the examples below, unless otherwise stated in a particular case,
a) all amounts refer to weight;
b) all pressures are 1013 hPa (atmospheric pressure);
c) all temperatures are 20° C.

COMPARATIVE EXAMPLE C1

In accordance with the teachings of U.S. Pat. No. 2,681,355, 180 ml/h of high-boiling silane-synthesis residue with a boiling point >150° C. was metered concurrently at room temperature and ambient pressure with 25 l/h of gaseous hydrogen chloride into a horizontal steel tube of length 700 mm and internal diameter 25 mm, without internals, located in a tube furnace. The tube furnace was adjusted to a temperature of 550° C. The high-boiling residue was composed of 80% of disilanes (mixture of 1,1,2,2-tetrachlorodimethyldisilane, 1,1,2-trichlorotrimethyldisilane and 1,2-dichlorotetramethyldisilane, 2% of solid fractions and 18% of siloxanes and carbosilanes. A more precise assignment is difficult because of the wide variety of byproducts. The experiment was terminated after 17 hours of operation due to the build-up of solids and cracking products in the reaction zone of the tubular reactor.

During the experiment, a cleaved silane was produced and had the composition shown in Table 1:

TABLE 1

| Substance | Proportion in cleaved silane [% by weight] |
|---|---|
| Dimethylchlorosilane | 1 |
| Methyldichlorosilane | 10 |
| Trimethylchlorosilane | 2 |
| Methyltrichlorosilane | 35 |
| Dimethyldichlorosilane | 32 |
| Solids | 3 |
| Others | 17 |

EXAMPLE 1

1500 ml/h of the silane-synthesis residue mixture from Comparative Example C1 and 170 l/h of gaseous hydrogen chloride were metered concurrently at room temperature and ambient pressure into a vertically arranged reactor (length 1000 mm, diameter 100 mm) incorporating a rigid three-bladed rotor. The reactor was heated to 600° C. by means of a tube furnace. Even after 50 hours of operation, only a small deposit was found on the internal wall of the reactor. A cleaved silane with the composition shown in Table 2 was produced in the experiment:

TABLE 2

| Substance | Proportion in cleaved silane [% by weight] |
|---|---|
| Dimethylchlorosilane | 2 |
| Methyldichlorosilane | 10 |
| Trimethylchlorosilane | 1 |
| Methyltrichlorosilane | 32 |
| Dimethyldichlorosilane | 33 |

TABLE 2-continued

| Substance | Proportion in cleaved silane [% by weight] |
|---|---|
| Solids | 3 |
| Uncleaved disilanes | 4 |
| Others | 15 |

What is claimed is:

1. A continuous process for preparing alkylchlorosilanes from the residues of direct synthesis of alkylchlorosilanes, said residues containing liquid constituents with a boiling point of at least 70° C. at 1013 hPa and further containing solids, said process comprising:

heating said residues with hydrogen chloride at temperatures of from 300° C. to 800° C. in a tubular reactor with internals which can be rotated.

2. A process as claimed in claim 1 in which heating is carried out at temperatures of from about 500° C. to about 650° C.

3. A process as claimed in claim 1 in which the pressure in the reactor is from about 1000 hPa to about 3000 hPa.

4. A process as claimed in claim 2 in which the pressure in the reactor is from about 1000 hPa to about 3000 hPa.

5. The process of claim 1 where in the mole equivalent ratio of hydrogen chloride to disilane is from about 1 to about 10.

6. The process of claim 1 wherein the mole equivalent ratio of hydrogen chloride to disilane is from about 1.1 to 2.

7. The process of claim 1 wherein said residue has a boiling point of 80° C.

8. The process of claim 1 wherein sintered particulates are removed from an exit stream from said reactor.

* * * * *